United States Patent
Searle et al.

(10) Patent No.: US 9,867,929 B2
(45) Date of Patent: Jan. 16, 2018

(54) PUMP ENGINE WITH METERING SYSTEM FOR DISPENSING LIQUID MEDICATION

(71) Applicants: Gary Searle, Norfolk, MA (US); Roman Tunkel, Burlington, MA (US); William Tormey, III, Buzzards Bay, MA (US); Andrew Leonczyk, Warwick, RI (US); David Pollock, Charlestown, RI (US); Paul Naumann, Medfield, MA (US); Kenneth Focht, Needham, MA (US)

(72) Inventors: Gary Searle, Norfolk, MA (US); Roman Tunkel, Burlington, MA (US); William Tormey, III, Buzzards Bay, MA (US); Andrew Leonczyk, Warwick, RI (US); David Pollock, Charlestown, RI (US); Paul Naumann, Medfield, MA (US); Kenneth Focht, Needham, MA (US)

(73) Assignee: Becton, Dickinson and Company, Frankling Lakes, NJ (US)

( * ) Notice: Subject to any disclaimer, the term of this patent is extended or adjusted under 35 U.S.C. 154(b) by 24 days.

(21) Appl. No.: 13/963,748

(22) Filed: Aug. 9, 2013

(65) Prior Publication Data
US 2014/0052096 A1    Feb. 20, 2014

Related U.S. Application Data

(60) Provisional application No. 61/683,488, filed on Aug. 15, 2012.

(51) Int. Cl.
*A61M 5/145*    (2006.01)
*A61M 5/142*    (2006.01)
*A61M 5/168*    (2006.01)

(52) U.S. Cl.
CPC ...... *A61M 5/14244* (2013.01); *A61M 5/1452* (2013.01); *A61M 5/16809* (2013.01);
(Continued)

(58) Field of Classification Search
CPC .......... A61M 2039/242; A61M 1/3641; A61M 1/3639; A61M 2205/15; A61M 2205/3331
(Continued)

(56) References Cited

U.S. PATENT DOCUMENTS 4,170,520 A * 10/1979 Weaver ................. C12M 21/18
435/287.1
4,250,887 A *  2/1981 Dardik .................. A61B 6/481
600/432

(Continued)

FOREIGN PATENT DOCUMENTS

EP        2019206 A1    1/2009
WO   2004032994 A2    4/2004
(Continued)

*Primary Examiner* — Imani Hayman
*Assistant Examiner* — Matthew A Engel
(74) *Attorney, Agent, or Firm* — Dickinson Wright, PLLC (57) ABSTRACT

An infusion pump system is disclosed for dispensing liquid medication, such as insulin. The infusion pump system includes a first reservoir for storing liquid medication, a first fluid driver for exerting pressure on the first reservoir, a second reservoir for storing liquid medication, and a second fluid driver for exerting pressure on the second reservoir. One or more valves are used to permit flow of liquid medication from the first reservoir to the second reservoir, and to permit flow of liquid medication from the second reservoir to an infusion site. Each of the valves is selectively opened or closed to fill the second reservoir with liquid medication from the first reservoir and to dispense liquid (Continued)

medication from the second reservoir to the infusion site. A controller and one or more sensors are used to monitor and control the system.

25 Claims, 9 Drawing Sheets (52) U.S. Cl.
CPC ............... *A61M 5/16881* (2013.01); *A61M 2005/16863* (2013.01); *F04C 2270/041* (2013.01)

(58) Field of Classification Search
USPC ....... 604/9, 67, 506, 32, 256, 248, 181–183, 604/167, 151
See application file for complete search history.

(56) References Cited

U.S. PATENT DOCUMENTS

| | | | |
|---|---|---|---|
| 4,854,324 A * | 8/1989 | Hirschman et al. | 600/432 |
| 5,002,528 A | 3/1991 | Palestrant | |
| 5,609,572 A * | 3/1997 | Lang | A61M 5/142 604/22 |
| 5,858,001 A | 1/1999 | Tsals et al. | |
| 5,858,005 A | 1/1999 | Kriesel | |
| 5,957,895 A | 9/1999 | Sage et al. | |
| 6,074,369 A | 6/2000 | Sage et al. | |
| 6,551,276 B1 | 4/2003 | Mann et al. | |
| 6,589,229 B1 * | 7/2003 | Connelly | A61M 5/14248 604/65 |
| 6,656,158 B2 | 12/2003 | Mahoney et al. | |
| 6,740,059 B2 * | 5/2004 | Flaherty | A61M 5/14248 600/151 |
| 6,852,104 B2 | 2/2005 | Blomquist | |
| 6,960,192 B1 | 11/2005 | Flaherty et al. | |
| 7,052,251 B2 | 5/2006 | Nason et al. | |
| 7,109,878 B2 | 9/2006 | Mann et al. | |
| 7,128,727 B2 | 10/2006 | Flaherty et al. | |
| 7,226,278 B2 | 6/2007 | Nason et al. | |
| 7,250,037 B2 | 7/2007 | Shermer et al. | |
| 7,303,549 B2 | 12/2007 | Flaherty et al. | |
| 7,678,079 B2 | 3/2010 | Shermer et al. | |
| 7,857,131 B2 | 12/2010 | Vedrine | |
| 8,021,334 B2 | 9/2011 | Shekalim | |
| 8,322,993 B2 * | 12/2012 | Adleff | A61M 5/145 204/600 |
| 8,323,237 B2 * | 12/2012 | Radmer | A61J 1/20 604/416 |
| 8,826,981 B2 * | 9/2014 | van Hal | E21B 49/081 166/250.12 |
| 8,920,376 B2 * | 12/2014 | Caffey | A61M 5/14526 204/630 |
| 9,320,851 B2 * | 4/2016 | Regittnig | A61M 5/16836 |
| 2002/0115933 A1 * | 8/2002 | Duchon | A61M 5/14216 600/432 |
| 2002/0165491 A1 * | 11/2002 | Reilly | A61M 5/14546 604/154 |
| 2005/0052509 A1 * | 3/2005 | Gilligan | B01L 3/50273 347/85 |
| 2005/0234428 A1 * | 10/2005 | Spohn | A61M 5/007 604/533 |
| 2005/0238536 A1 * | 10/2005 | Striepeke | G01N 33/50 422/68.1 |
| 2008/0015494 A1 * | 1/2008 | Santini et al. | 604/65 |
| 2008/0086111 A1 | 4/2008 | Cowan | |
| 2008/0097381 A1 | 4/2008 | Moberg et al. | |
| 2009/0048563 A1 | 2/2009 | Ethelfeld et al. | |
| 2009/0062778 A1 | 3/2009 | Bengtsson et al. | |
| 2009/0112155 A1 * | 4/2009 | Zhao et al. | 604/67 |
| 2009/0129945 A1 * | 5/2009 | Adleff | A61M 5/145 417/53 |
| 2009/0149743 A1 | 6/2009 | Barron | |
| 2009/0204066 A1 * | 8/2009 | Radmer | A61J 1/20 604/86 |
| 2010/0042068 A1 * | 2/2010 | Friebe | A61M 5/007 604/506 |
| 2010/0145303 A1 * | 6/2010 | Yodfat | A61M 5/1408 604/506 |
| 2011/0054397 A1 * | 3/2011 | Menot et al. | 604/110 |
| 2011/0186177 A1 * | 8/2011 | Lanier, Jr. | A61J 1/2065 141/383 |
| 2011/0190694 A1 * | 8/2011 | Lanier, Jr. | A61M 5/14216 604/67 |
| 2011/0230838 A1 | 9/2011 | Adams | |
| 2013/0075093 A1 * | 3/2013 | van Hal | E21B 49/081 166/264 |
| 2013/0178826 A1 * | 7/2013 | Li | A61M 5/155 604/506 |

FOREIGN PATENT DOCUMENTS

| | | |
|---|---|---|
| WO | 2008040812 A1 | 4/2008 |
| WO | WO-2011082272 | 7/2011 |
| WO | 2012069308 A1 | 5/2012 |
| WO | 2012126744 A1 | 9/2012 |

* cited by examiner

PUMP ENGINE WITH METERING SYSTEM FOR DISPENSING LIQUID MEDICATION

CROSS-REFERENCE TO RELATED APPLICATION

This application claims the benefit under 35 U.S.C. § 119(e) of U.S. Provisional Application No. 61/683,488, filed on Aug. 15, 2012 in the U.S. Patent and Trademark Office, the disclosure of said application being incorporated herein by reference in its entirety.

FIELD OF THE INVENTION

The present invention relates generally to a fail-safe metering system for a pump engine or fluid driver that provides improved dosing accuracy for insulin and other liquid medications.

BACKGROUND OF THE INVENTION

Diabetes is a group of diseases marked by high levels of blood glucose resulting from defects in insulin production, insulin action, or both. Diabetes can lead to serious health complications and premature death, but there are well-known products available for people with diabetes to help control the disease and lower the risk of complications.

Treatment options for people with diabetes include specialized diets, oral medications and/or insulin therapy. The primary goal for diabetes treatment is to control the patient's blood glucose (sugar) level in order to increase the chances of a complication-free life. It is not always easy, however, to achieve good diabetes management, while balancing other life demands and circumstances.

Currently, there are two principal modes of daily insulin therapy for the treatment of type 1 diabetes. The first mode includes syringes and insulin pens that require a needle stick at each injection, typically three to four times per day. These devices are simple to use and relatively low in cost. Another widely adopted and effective method of treatment for managing diabetes is the use of an insulin pump. Insulin pumps can help users keep their blood glucose levels within target ranges based on their individual needs, by providing continuous infusion of insulin at varying rates to more closely mimic the behavior of the pancreas. By using an insulin pump, users can match their insulin therapy to their lifestyles, rather than matching their lifestyles to how an insulin injection is working for them.

Conventional insulin pumps are capable of delivering rapid or short-acting insulin 24 hours a day through a cannula (typically a hollow metal needle or a flexible plastic catheter) placed under the skin. Insulin doses are typically administered at a basal rate and in a bolus dose. Basal insulin is delivered continuously over 24 hours, and strives to keep one's blood glucose levels in a consistent range between meals and overnight. Some insulin pumps are capable of programming the basal rate of insulin to vary according to the different times of the day and night. Bolus doses are typically administered when the user consumes a meal, and generally provide a single additional insulin injection to balance the carbohydrates consumed. Some conventional insulin pumps enable the user to program the volume of the bolus dose in accordance with the size or type of the meal consumed. Conventional insulin pumps also enable a user to infuse a correctional or supplemental bolus of insulin to compensate for a low blood glucose level at the time the user is calculating a meal bolus.

There are many advantages of conventional insulin pumps over other methods of diabetes treatment. Insulin pumps deliver insulin over time rather than in single injections and thus typically result in less variation within the blood glucose range that is recommended by the American Diabetes Association. Conventional insulin pumps may reduce the number of needle sticks which the patient must endure, and may make diabetes management easier and more effective for the user, to enhance the quality of the user's life. Typically, regardless of whether patients are on multiple direct injections (MDIs) or a pump, they take fasting blood glucose medication (FBGM) when they wake, and they also test for glucose in the blood during or after each meal to determine whether a correction dose is required. In addition, patients may test for glucose in the blood prior to sleeping to determine whether a correction dose is required, e.g. after intake of a snack.

There are generally two types of insulin pumps: conventional pumps and patch pumps.

Conventional pumps require the use of a disposable component, typically referred to as an infusion set, tubing set or pump set, which conveys the insulin from a reservoir within the pump into the skin of the user. An infusion set typically consists of a pump connector, a length of tubing, and a hub or base from which a hollow metal infusion needle or flexible plastic catheter extends. The base has an adhesive that retains the base on the skin surface during use. The base may be applied to the skin manually or with the aid of a manual or automatic insertion device. Often, the insertion device is a separate, stand-alone unit that the user is required to carry and provide.

Another type of insulin pump is a patch pump. Unlike a conventional infusion pump and infusion set combination, a patch pump is an integrated device that combines most or all of the fluidic components (including the fluid reservoir and pumping mechanism) in a single housing which is adhesively attached to an infusion site, and does not require the use of a separate infusion (tubing) set. A patch pump adheres to the skin, contains insulin (or other medication), and delivers the insulin over a period of time via an integrated subcutaneous cannula. Some patch pumps communicate with a separate controller device wirelessly (as in one device sold by Insulet Corporation under the brand name OmniPod®), while others are completely self-contained. These devices usually need to be replaced on a frequent basis, such as every three days, when the reservoir is exhausted or complications may otherwise occur.

Figure 1:
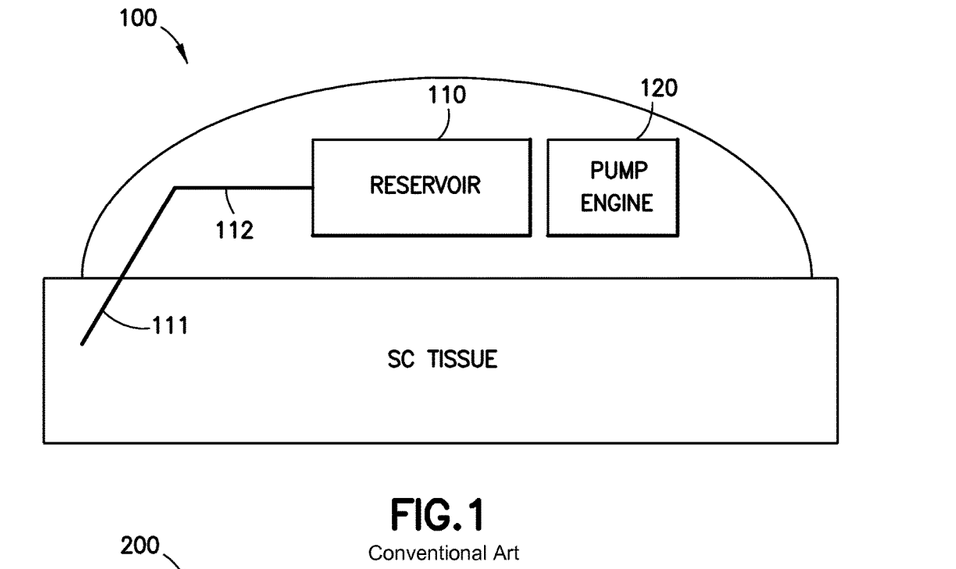
FIG. 1 depicts an illustrative embodiment of the basic elements of an insulin infusion patch pump.

An exemplary insulin patch pump 100 is shown in FIG. 1. The patch pump utilizes a single reservoir 110 that retains a full dose requirement for the duration of the pump device, which is typically 3 days. A pump engine 120 or other fluid driver typically applies force directly to the single reservoir 110, either through a secondary element, such as a plunger, or by direct deformation of the reservoir 110. This causes insulin to flow out of the reservoir 110 via the fluid line 112 and the cannula 111 and into the subcutaneous (SC) tissue of the patient.

Figure 2:
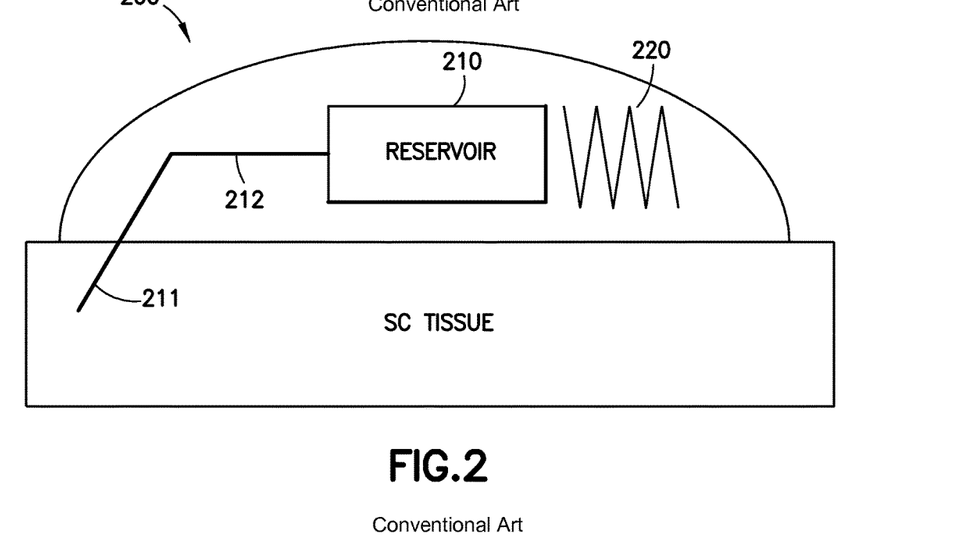
FIG. 2 depicts an illustrative embodiment of an insulin infusion patch pump having a preloaded spring as the pump engine.

In another type of patch pump 200, a simple form of a fluid driver is a preloaded spring 220, as shown in FIG. 2. In insulin patch pumps utilizing a preloaded spring 220, the continuous flow rate of insulin into the subcutaneous tissue is controlled only by a calibrated limiting orifice in the fluid line 212 or cannula 211, and the spring force applied to the reservoir 210 by the preloaded spring 220.

Shortcomings of this type of pump include spring force decay along the spring path resulting in flow rate decay, and spring force variation over the shelf life of the pump engine.

Additionally, this type of insulin pump lacks a "fail-safe" or means of protecting the patient from accidentally receiving an entire reservoir volume or delivering the entire reservoir content.

Figure 3:
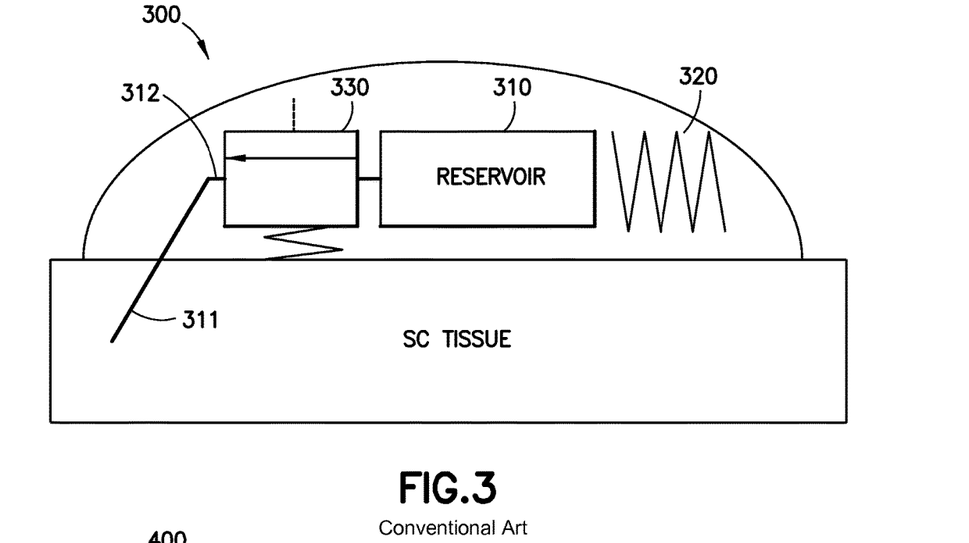
FIG. 3 depicts an illustrative embodiment of an insulin infusion patch pump with a preloaded spring pump engine and a directional control valve.

Alternatively, in another type of patch pump 300, the flow rate of insulin into the subcutaneous tissue can be discontinuous by incorporating a directional control valve 330, such as an on/off valve, into the fluid line 312 to provide infusion via the cannula 311 when required, as shown in FIG. 3. However, the valve 330 when used with a fluid driver 320 could still fail in the open position, resulting in a single point failure which would allow the full dose of drug to be infused into the patient. For example, if the valve 330 shown in FIG. 3 fails, the fluid path remains open and the pressurized reservoir 310 will be completely infused into the patient.

Figure 4:
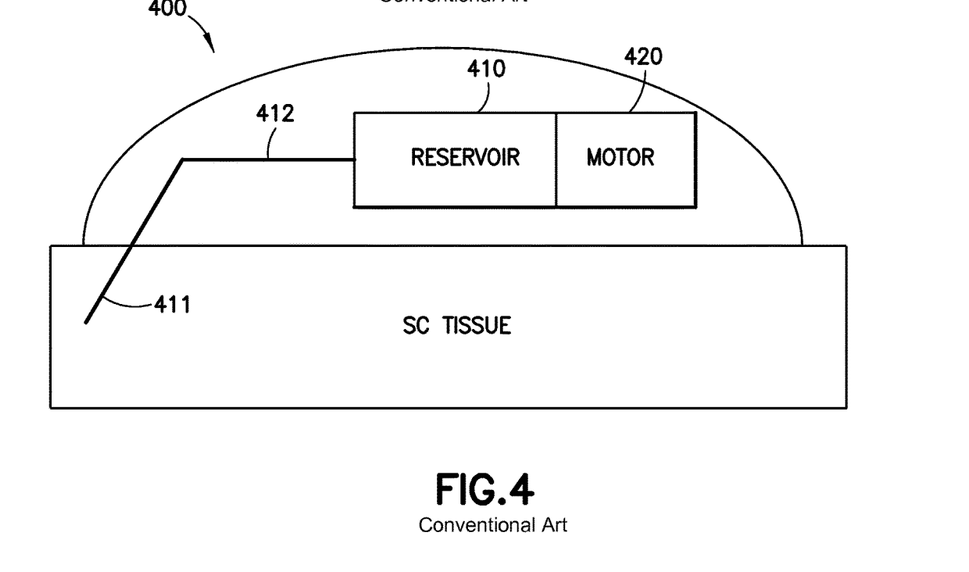
FIG. 4 depicts an illustrative embodiment of an insulin infusion patch pump having a stepper motor as the pump engine.

FIG. 4 illustrates another patch pump 400 for the treatment of diabetes. The illustrated fluid driver is a pump engine or motor 420. This device is typically a stepper motor or other device that behaves similarly, such as a mechanism that advances a small incremental dose from a syringe-style reservoir 410 to the infusion site via the fluid line 412 and the cannula 411, as shown in FIG. 4. The illustrated device provides a superior form of insulin therapy as compared with Multiple Daily Injections (MDIs), which is the prevalent method of insulin therapy for both type 1 and type 2 diabetes. The current trend for basal delivery in the industry is to pump smaller incremental doses over the target duration and thereby approach continuous infusion. Smaller incremental doses are also more suitable for pediatric applications.

Dosing accuracy is still a concern with the current trend of pump engines. Applicable standards, such as IEC 60601-2-24, require dose accuracy to be within +/−5% of target, creating difficulty for conventional volumetric pumps, which push a plunger by extremely small linear translations, approximately 2 micrometers per step.

Figure 5A:
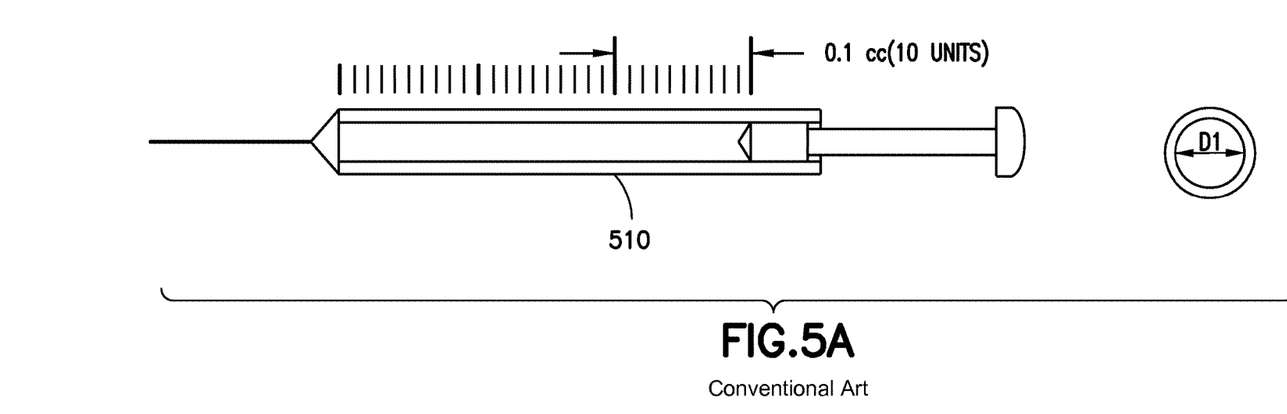
FIG. 5A depicts a cross-sectional and an end view of an illustrative embodiment of a 3/10 cc syringe.
Figure 5B:
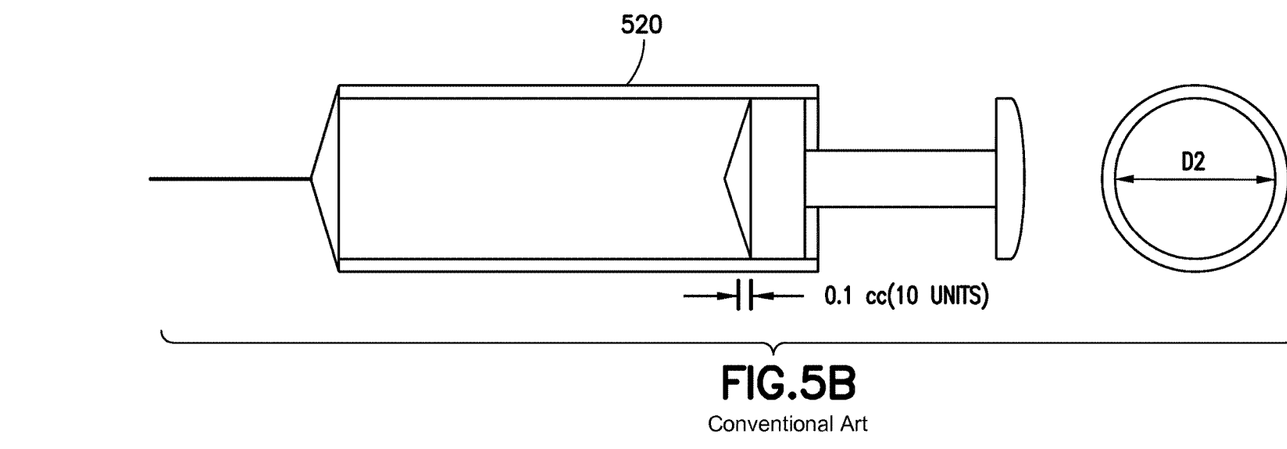
FIG. 5B depicts a cross-sectional and an end view of an illustrative embodiment of a 3 ml syringe.

For injections, higher accuracy can be provided by reducing the syringe diameter so that the same linear translation of the syringe plunger provides a smaller dose. For example, the same incremental movement of the plunger in a 3/10 cc syringe 510 having an inner diameter D1 of 0.338 inch, as illustrated in FIG. 5A, provides one-eighth the dose for the same incremental movement as compared to a 3 ml syringe 520 or eight times the accuracy of a 3 ml syringe 520 having an inner diameter D2 of 0.110 inch, as illustrated in FIG. 5B. The higher accuracy of the 3/10 cc syringe 510 may eliminate or reduce dosing errors and enables the use of higher concentration drugs, such as U200 and U500 insulin, which is often prescribed for patients with type 2 diabetes.

Accordingly, there is a need for a fail-safe metering system for a fluid driver or pump engine that incorporates the improved dosing accuracy of a smaller syringe diameter and protects the patient from inadvertently receiving an overdose of medicament.

Additionally, there is a need for a low cost metering system that can operated with any fluid driver or pump engine, including a completely disposable pumping system such as a patch pump.

SUMMARY OF THE INVENTION

An object of the present invention is to substantially address the above and other concerns, and provide higher levels of infusion accuracy in combination with a fail-safe metering system for an infusion pump that delivers insulin or other liquid medication.

Another object of the present invention is to address the inadvertent overdosing of a patient by only pre-loading and pressurizing a safe or less-than-harmful dose of medicament in the reservoir of the metering system in the insulin infusion pump.

Another object of the present invention is to provide a metering system that permits the use of higher concentration drugs while abiding by industry requirements for pump engine accuracy.

Another object of the present invention is to provide a metering system that permits fine incremental dosing to approximate continuous infusion.

Another object of the present invention is to provide a low-cost metering system that can be integrated as part of an infusion pump device with any type of fluid driver or pump engine, including pump engines with low or poor accuracy.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawing figures, like reference numbers will be understood to refer to like elements, features and structures.

DETAILED DESCRIPTION OF THE EXEMPLARY EMBODIMENTS

Embodiments of the present invention relate to a fail-safe metering system for a pump engine or fluid driver that provides improved insulin dosing accuracy for insulin and other liquid medications.

Figure 6:
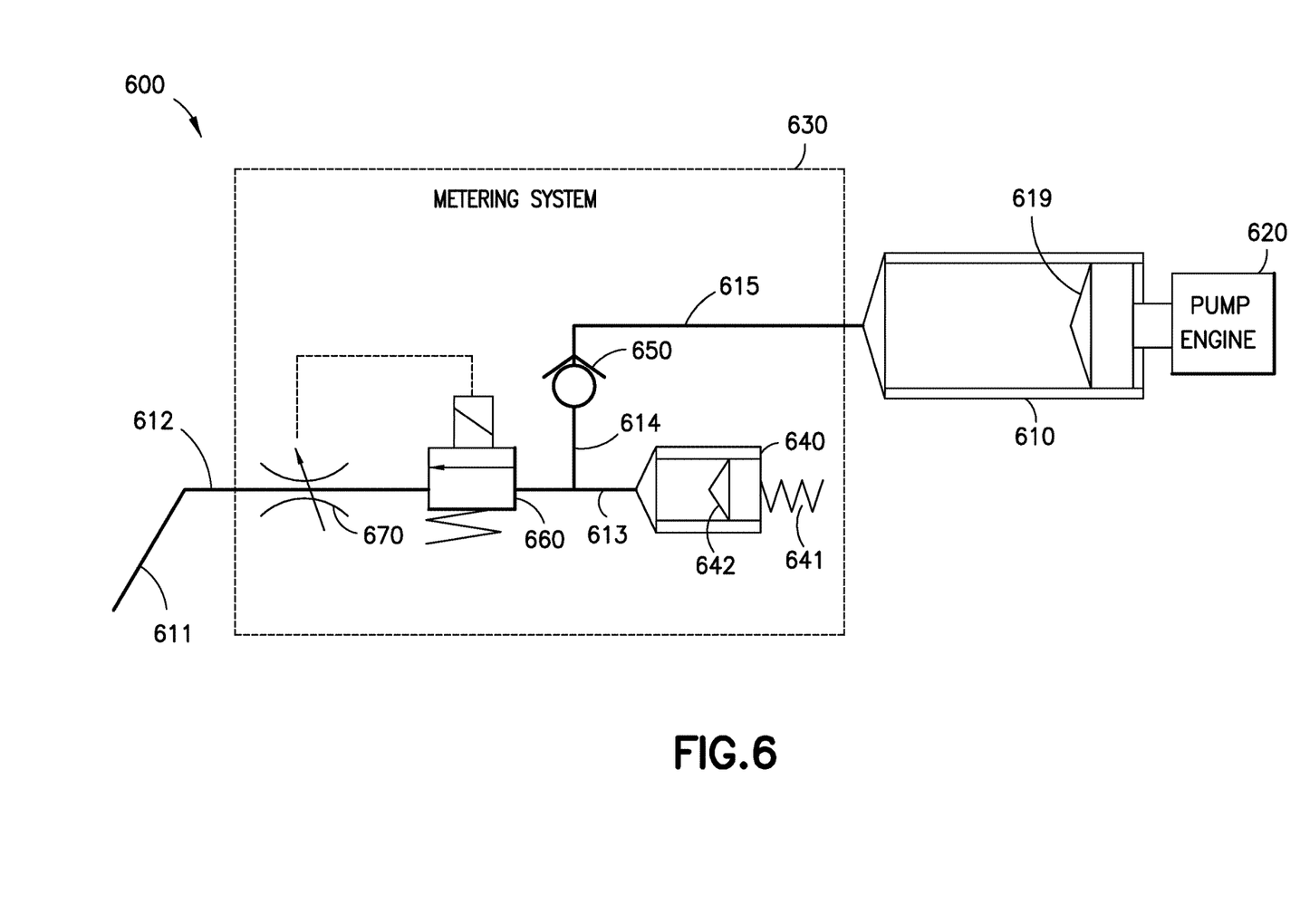
FIG. 6 depicts an illustrative embodiment of an insulin infusion metering system of the present invention connected to a primary pump engine.

An illustrative embodiment of the components of a fail-safe metering pump system 600 according to the present invention is shown in FIG. 6. Referring to FIG. 6, the infusion pump system generally includes a fluid driver in the form of a pump engine 620, a primary reservoir 610, and a metering system 630 including a secondary reservoir 640, at least one check valve 650, at least one directional control valve 660, and an adjustable flow valve 670. In another embodiment described herein, the adjustable flow valve 670 is replaced by a calibrated limiting orifice. In yet another embodiment, the check valve(s) 650 is replaced by the directional control valve(s) 670. Fluid lines 612, 613, 614 and 615 connect the various components of the system, as illustrated in FIG. 6.

The pump engine 620 of the illustrative embodiments of the present invention is interchangeable. The pump engine 620 may be a spring-driven pump, stepper motor driven pump, an electrochemical pump, an electro-osmotic pump, or any positive pressure pump.

The primary reservoir 610 or macro-reservoir is a bulk fluid storage chamber for storing and dispensing a medicament, such as insulin, and may comprise a 3 ml syringe. The dosing accuracy of the primary reservoir's pump engine 620 could be anywhere within +/−10% of target dose.

The secondary reservoir 640 or micro-reservoir is provided to limit inadvertent insulin delivery by only pre-loading and pressurizing a safe or less-than-harmful dose of insulin medicament within the secondary reservoir 640. A fluid driver 641, which can be a preloaded spring, solenoid, or other type of fluid driver, delivers incremental micro-doses from the secondary reservoir via plunger 642 to the infusion site.

The check valve 650 is provided to eliminate flow back to the primary reservoir during the secondary reservoir delivery cycle. In an exemplary embodiment, as exemplified in FIG. 6, the pump engine 620 applies pressure to a plunger 619 to expel insulin from the primary reservoir 610 into the fluid line 615, opening the check valve 650, until the insulin has been transferred to the secondary reservoir 640.

The directional control valve 660 controls the isolation of the fluid path when filling or dispensing from the secondary reservoir 640. The directional control valve 660 is electrically controlled and is normally closed to prevent unintentional delivery of insulin to the infusion site. Embodiments of the directional control valve 660 include, but are not limited to, isolation valves such as gate valves, pinch valves, spool valves or the like.

The opening of the normally closed directional control valve 660 enables insulin to flow to the infusion site with the flow rate controlled by the adjustable flow valve 670. A controller (not shown in FIG. 6) calculates the duration for which the directional control valve 660 remains open based on the pressure being applied to the insulin in the secondary reservoir 640 by the fluid driver 641 and the opening/orifice in the adjustable flow valve 670. That is, the controller converts the patient's dose requirements into flow rate and duration settings.

The operation of the fail-safe metering pump system 600 shown in FIG. 6 is discussed below.

When the fluid level in the secondary reservoir 640 is low, the pump engine 620 is activated to transfer insulin from the primary reservoir 610 to the secondary reservoir 640. With the check valve 650 in an open position and the adjustable flow valve 670 in a closed position, insulin is permitted to flow through fluid lines 613, 614 and 615 into the secondary reservoir 640 from the primary reservoir 610. Check valves, such as the check valve 650, are typically spring loaded N/C (normally closed) valves in which a ball is engaged into a seat in a manner that blocks downstream flow through the orifice in the seat. Hence, when the line pressure opposing the ball increases beyond the rated cracking pressure of the check valve, the ball dislodges from the seat allowing downstream flow through the orifice in the seat. The opening and closing of check valve 650 occurs when the pump engine 620 moves the plunger 619, creating a positive pressure in the fluidic line 615 that is greater than the cracking pressure in the check valve 650, and the pressure in fluidic line 614/613, which is generated by the fluid driver 641.

When a pump controller of the system 600 receives a signal to provide insulin, the directional control valve 660 opens, while the check valve 650 is in a closed position, to allow flow to the infusion site via the fluid line 612 and a hollow metal needle or flexible plastic catheter 611 with the flow rate controlled by the adjustable flow valve 670. Embodiments of the adjustable flow valve 670 include, but are not limited to, control valves that modulate flow by varying the diameter of the opening by a certain percentage, such as diaphragm valves or the like.

In this embodiment, the line pressure, which is the pressure applied to the secondary reservoir 640 by the fluid driver 641, such as a preloaded spring, is known and the flow of insulin is regulated depending on the dose requirement for basal or bolus. The dose delivered is a function of the line pressure, the duration for which the directional control valve 660 is open, and the variable limiting orifice in the adjustable flow valve 670. Ambient temperature and atmospheric pressure could also be factored into the infusion dose calculation to further improve dose accuracy.

The dosing accuracy of the metering system 630 with the secondary reservoir 640 of illustrative embodiments of the present invention provides higher levels of infusion accuracy that can be within +/−1% of the target dose regardless of the pump engine chosen for the primary reservoir, while preventing the inadvertent overdosing of a patient by only pre-loading and pressurizing a safe or less-than-harmful dose of medicament in the secondary reservoir 640 of the metering system 630.

Illustrative embodiments of the metering system infusion pump device 600 of the present invention may include, but are not limited to, sensors for detecting occlusion or back pressure within the infusion pump device, sensors for detecting bubbles in the delivery line of the infusion pump device, sensors for detecting the fill status of the secondary reservoir 640 of the infusion pump device 600, including the end of the secondary reservoir 640 or insulin remaining in the secondary reservoir 640, sensors for detecting leakage in the infusion pump device 600, and sensors for measuring the flow rate of the insulin or other medications.

Figure 7:
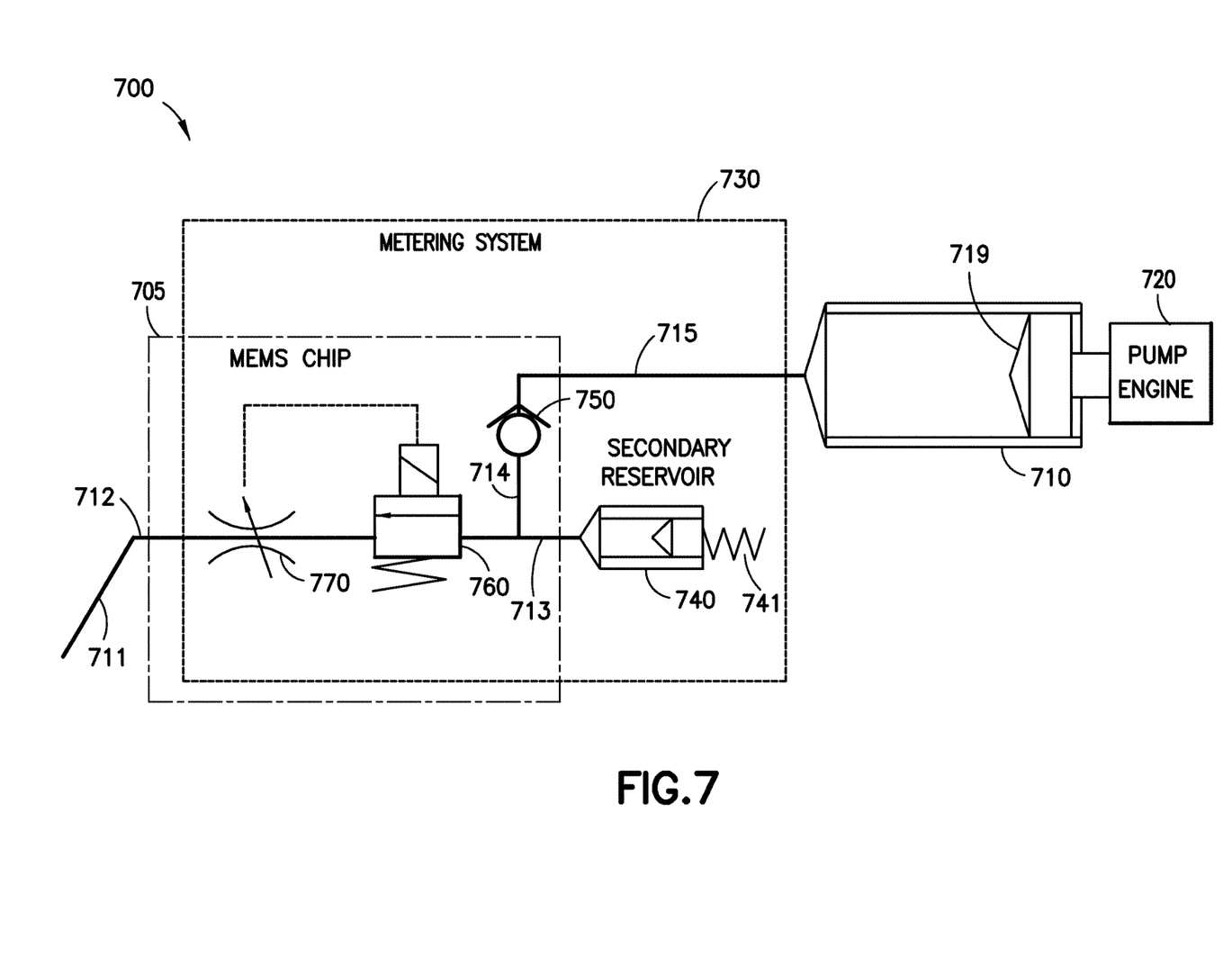
FIG. 7 depicts an illustrative embodiment of an insulin infusion metering system of the present invention incorporated into a Micro Electro Mechanical Systems (MEMS) chip.

Referring to FIG. 7, an infusion pump system 700 in accordance with another illustrative embodiment of the present invention combines the sensors and elements of the metering system 730 of the infusion pump, as in the embodiment of FIG. 6, such as the check valve 750, the directional control valve 760 and the adjustable flow valve 770, into a Micro Electro Mechanical Systems (MEMS) chip 705 that is connected to the primary reservoir 710 and the secondary reservoir 740 via the fluid lines 713, 714 and 715.

Combining these components into a MEMS chip 705 is a low-cost and efficient way to provide many of the metering system components and the sensing elements typically required in an insulin infusion pump in a smaller package, thus reducing the overall size of the infusion pump device.

In the infusion pump system 700, when the fluid level in the secondary reservoir 740 is low, the pump engine 720 is activated to transfer insulin from the primary reservoir 710 to the secondary reservoir 740 by moving the plunger 719 within the reservoir 710. With the check valve 750 in an open position and the adjustable flow valve 770 in a closed position, insulin is forced to flow through fluid lines 713, 714 and 715 into the secondary reservoir 740 from the primary reservoir 710. When a pump controller of the system 700 receives a signal to provide insulin, the directional control valve 760 opens, while the check valve 750 is in a closed position, to allow flow of the insulin from the pressurized secondary reservoir 740 to the infusion site via the fluid line 712 and into the hollow needle or catheter 711, with the flow rate being controlled by the adjustable flow valve 770. The fluid driver 741 can deliver incremental micro-doses from the secondary reservoir 740 to the infusion site.

Figure 8:
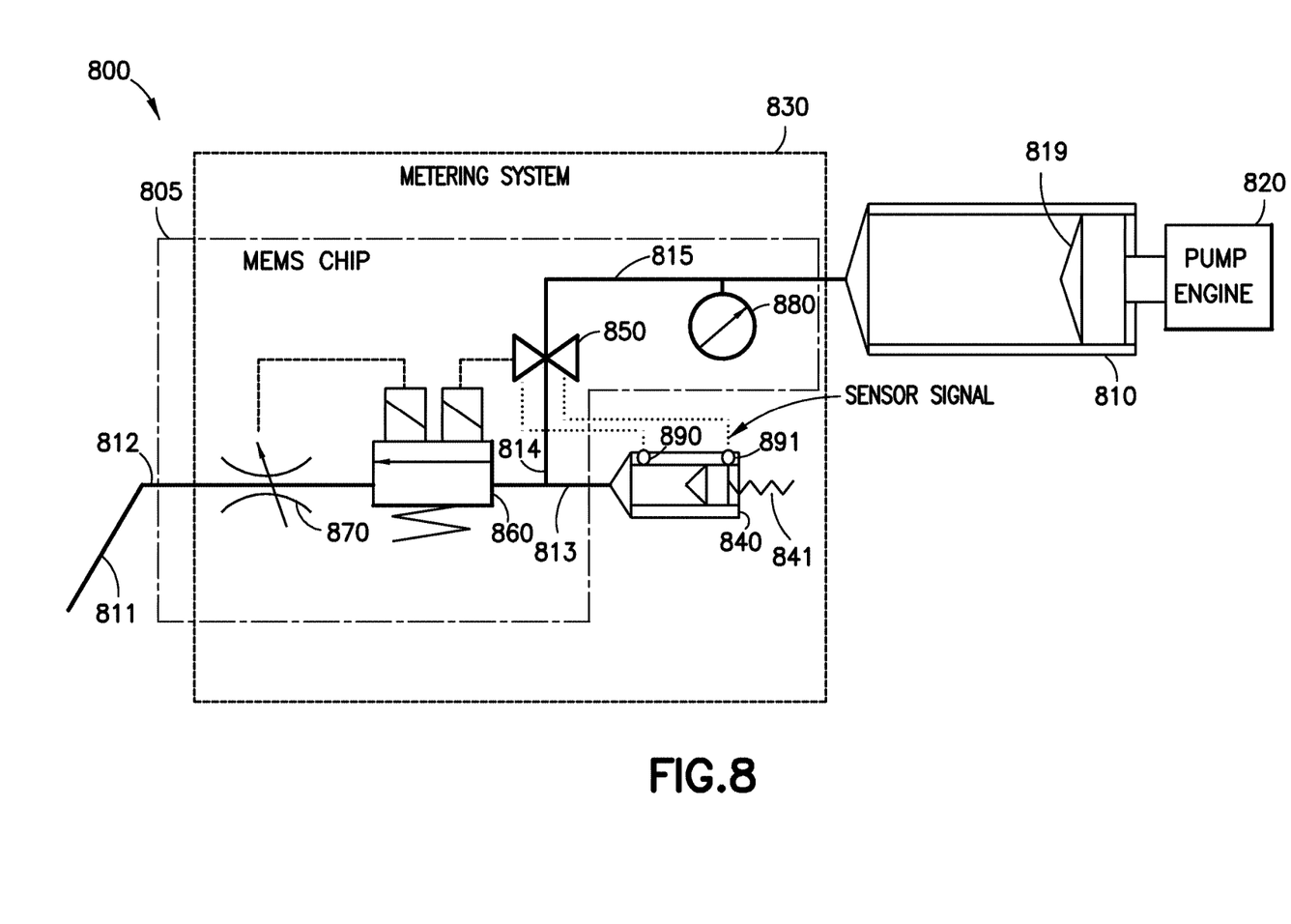
FIG. 8 depicts an illustrative alternate embodiment of an insulin infusion metering system of the present invention incorporating a MEMS chip.

Infusion pump system 800 is another illustrative embodiment of the present invention incorporating metering system elements of an infusion pump device into a MEMS chip 805 and is shown in FIG. 8. Referring to FIG. 8, the fluid delivery system 800 generally includes a pump engine 820 a primary reservoir 810, and a metering system 830 including a secondary reservoir 840, a fluid driver 841, a flow control valve 850, a directional control valve 860, an adjustable flow valve 870, a pressure sensor 880, and two position sensors 890, 891.

The pump engine 820 of illustrative embodiments of the present invention is interchangeable and may be a spring-driven pump, a stepper motor driven pump, an electrochemical pump, an electro-osmotic pump, or any positive pressure pump.

The primary reservoir 810 or macro-reservoir is a bulk fluid storage chamber for storing and dispensing insulin or other medicament, and may comprise a 3 ml syringe. The dosing accuracy of pump engine 820 could vary within +/−10% of the target dose.

The secondary reservoir 840 or micro-reservoir of the metering system 830 is provided to limit inadvertent insulin delivery by only pre-loading and pressurizing a safe or less-than-harmful dose of insulin medicament within the secondary reservoir 840. A fluid driver 841 in the form of a preloaded spring, stepper motor, or other fluid driver delivers incremental micro-doses from the secondary reservoir 840. One or more position sensors 890, 891 are connected to the secondary reservoir 840. The position sensors 890, 891 provide feedback to the pump controller on the fill status of the secondary reservoir 840.

The flow control valve 850 controls the insulin flow from the primary reservoir 810 to the secondary reservoir 840 via the fluid lines 813, 814 and 815. The flow control valve 850 opens to fill the secondary reservoir 840 with insulin from the primary reservoir 810. The flow control valve 850 allows partial delivery to the secondary reservoir 840, which allows increased dosing accuracy and the option of a larger secondary reservoir 840. Moreover, by using the flow control valve 850, a simple pump engine, such as a spring/elastic actuator or membrane, or any constant pressurized mechanism such as a gas actuator, may be utilized in the fluid delivery system 800. Refilling of the secondary reservoir 840 occurs between the incremental dose delivery to the patient, i.e., when insulin is not being delivered to the patient.

The directional control valve 860 controls the isolation of the fluid path, between the fluid lines 812 and 813, when dispensing from the secondary reservoir 840. The directional control valve 860 is provided to prevent unintentional delivery of insulin to the infusion site by permitting the flow of insulin only when required to satisfy the patient's insulin requirement and only in the direction of the arrow on the valve 860, illustrated in FIG. 8, from fluid line 813 into fluid line 812.

The opening of the directional control valve 860 enables insulin to flow to the infusion site with the flow rate controlled by the adjustable flow valve 870.

The pressure sensor 880 is used for sensing and monitoring the line pressure and can generate a signal to the pump controller confirming that the secondary reservoir 840 is filled in order to stop the pump engine 820 from pumping additional insulin to the secondary reservoir 840. The single pressure sensor 880 is used to detect pressure decay, and by opening the valves 850, 860 and 870 sequentially, the single sensor 880 can determine where in the fluidic system a leak may exist, the fill state of both the primary reservoir 810 and the secondary reservoir 840, and whether partial or complete occlusion exists. Alternately, the position sensors 890, 891 can be used for this purpose, and the pressure sensor 880 can be utilized to determine leakage in the system.

The illustrative embodiment of the present invention in FIG. 8 combines the sensors and elements of the metering system, such as the flow control valve 850, the directional control valve 860, the adjustable flow valve 870 and the pressure sensor 880, into a Micro Electro Mechanical Systems (MEMS) chip 805 that is connected to the reservoirs 810 and 840.

The operation of the infusion pump system incorporating metering system elements into MEMS chip 805 will be discussed with continued reference to FIG. 8.

The pump engine 820, via the primary reservoir 810, is activated temporarily by a pump controller (not shown in FIG. 8) to fill the secondary reservoir 840 with insulin by opening the flow control valve 850 whenever the fluid level in the secondary reservoir 840 is low according to an electrical signal sent by the position sensors 890, 891 connected to the secondary reservoir 840.

Once the secondary reservoir 840 is full, the filled status of the secondary reservoir 840 is confirmed to the pump controller by the duration of the refill cycle, or by feedback from the pressure sensor 880, or with an electrical signal from the position sensors 890, 891 connected to the secondary reservoir 840. The signal from the position sensor 891 is transmitted to the pump controller of the system 800 to close the flow control valve 850 and stop the pump engine 820 from pumping insulin from the primary reservoir 810. Alternately, the pressure sensor 880 can generate a similar signal to stop the pump engine 820 from pumping insulin from the primary reservoir 810, when the secondary reservoir 840 is filled either independently, when the pressure sensed has stabilized, or in conjunction with a second pressure sensor (not shown) located in the downstream fluidic line 813 or 814.

The secondary reservoir 840 can be of the same size as the smallest incremental dose requirement, e.g. 0.5 µL/0.25 µL, such that one complete evacuation cycle of the secondary reservoir will deliver 0.5 µL/0.25 µL to the patient. Due to the small diameter of the secondary reservoir 840, when the same linear translation of the syringe plunger provides a smaller dose, dosing accuracy is improved to within +/−1% of the target dose. Additionally, due to the relatively small geometry of the secondary reservoir 840, a maximum dose that can be delivered from a system failure is small, thus providing a fail-safe that prevents the patient from receiving an overdose of insulin. To deliver a large dose to a patient, such as bolus, multiple incrementing doses (equal or smaller than the volume of the secondary reservoir 840) are required.

Incremental dosing of insulin from the secondary reservoir 840 is facilitated by the opening of the directional control valve 860, which enables insulin flow from the pressurized secondary reservoir 840 to the infusion site, via the fluid line 812 and into the hollow needle or catheter 811. The flow rate of the insulin is controlled by the adjustable flow valve 870.

When complete delivery of the insulin dose from the secondary reservoir 840 is sensed by the position sensors 890, 891, the pump controller of the system 800 closes the directional control valve 860 and opens the flow control valve 850, thus repeating the cycle of filling the secondary reservoir 840 after each individual cycle. In addition, the presence of the pressure sensor 880 at fluid line 815 allows the fluid delivery system 800 to determine how much medication was filled in the primary reservoir 810, since the sensed pressure is proportional to the displacement or position of the plunger 819 in the primary reservoir 810.

Consistent with the other described embodiments of the present invention, only one valve needs to be open at a time. For example, to transfer insulin from the primary reservoir 810 to the secondary reservoir 840, the flow control valve 850 is opened and the directional control valve 860 is closed. To infuse insulin into the patient, the flow control valve 850 is closed and the directional control valve 860 is open. At no time during the duration of use of the patch pump 800 are both valves 850 and 860 simultaneously opened. In addition, it is possible to combine the functions of the valves. For instance, the directional control valve 660, 760, 860 can be incrementally adjustable such that it can achieve the function of the adjustable flow valve 670, 770, 870. In such an embodiment, the adjustable flow valve 670, 770, 870 can be omitted.

Syringe-type reservoirs are shown in FIGS. 6-8, but the reservoirs utilized in the instant invention can be rigid or flexible and the configuration can vary depending on the pump engine selected.

Figure 9:
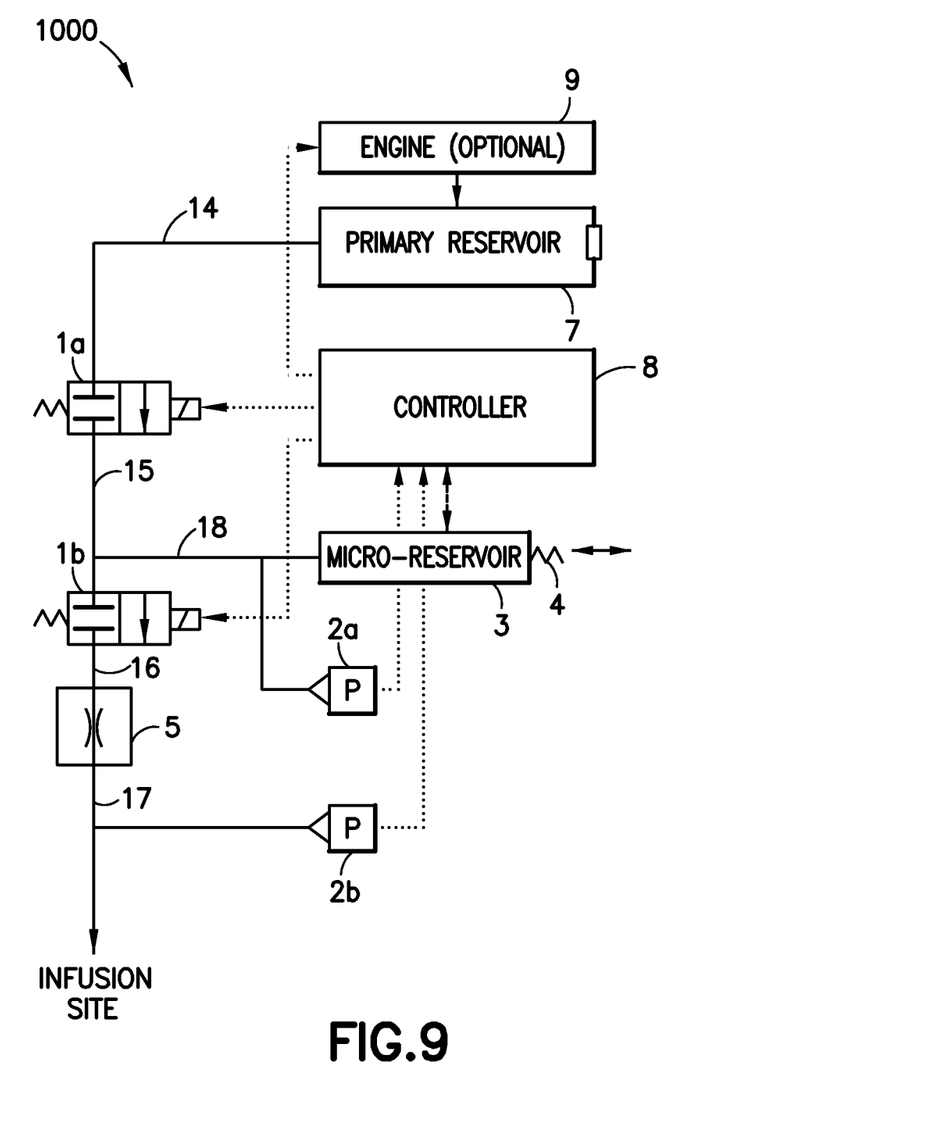
FIG. 9 depicts another illustrative alternate embodiment of an insulin infusion metering system of the present invention incorporating a MEMS chip.
Figure 10:
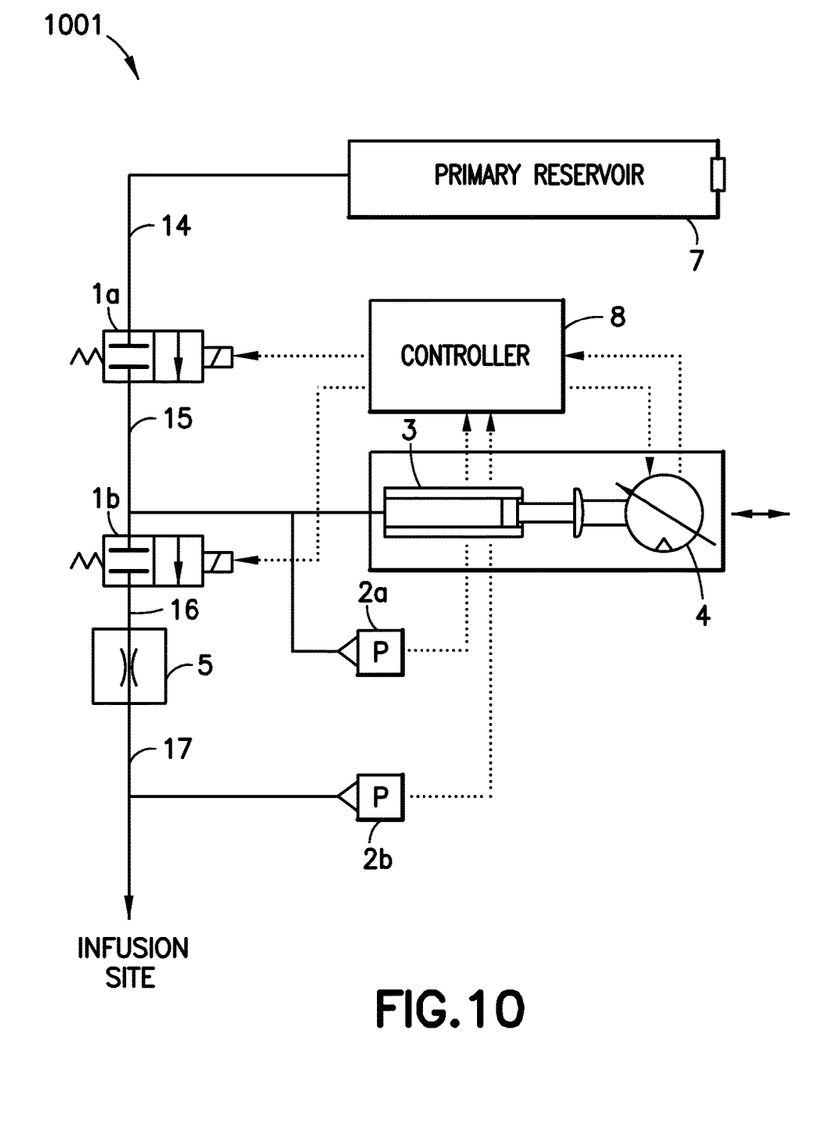
FIG. 10 depicts another illustrative alternate embodiment of an insulin infusion metering system of the present invention incorporating a MEMS chip.

Additional illustrative embodiments of the present invention incorporating metering system elements of an infusion pump device into a MEMS chip are shown in FIGS. 9 and 10. FIG. 9 illustrates a metering system for an infusion pump device incorporated into a MEMS chip with an energized reservoir. FIG. 10 illustrates a metering system for an infusion pump device incorporated into a MEMS chip with the micro-reservoir or secondary reservoir filled and emptied by a linear actuator.

Referring to FIG. 9, the metering system 1000 generally includes a primary reservoir 7, a micro-reservoir 3 with engine or driver 4, pressure sensors 2a, 2b, a controller 8, first and second N/C (normally closed) flow control valves 1a and 1b, a controlled orifice 5, and fluidic interconnects or fluid lines 14-18. FIG. 10 also shows a pump engine 9 or other fluid driver for the primary reservoir 7.

The pump engine 9 in illustrative embodiments of the present invention is optional and interchangeable, and may be a spring-driven pump, a stepper motor driven pump, an electrochemical pump, an electro-osmotic pump, or the like.

The primary reservoir 7 is a bulk fluid chamber for storing and dispensing insulin medicament, and may comprise a 3 ml syringe-style reservoir. The secondary reservoir or micro-reservoir 3 of the metering system is provided to limit inadvertent insulin delivery by pre-loading and pressurizing only a safe or less-than-harmful dose of insulin medicament within the micro-reservoir 3. A preloaded spring 4, or other fluid driver delivers incremental micro-doses from the micro-reservoir 3 to the infusion site.

One or more pressure sensors 2a, 2b are connected to the micro-reservoir 3. The pressure sensors 2a, 2b provide feedback to the pump controller 8 on the fill status of the micro-reservoir 3, detect occlusion or back pressure in the infusion pump device, detect leakage in the infusion device, and detect the injection flow rate of the insulin in the infusion pump device by measuring the pressure in the fluid lines 17 and 18.

The pump controller 8 interfaces with the pressure sensors 2a, 2b and actuates various components of the metering system of the present invention, such as the flow control valves 1a and 1b, and can also interface with a host computer or wireless controller (not shown).

The first N/C flow control valve 1a controls the insulin flow from the primary reservoir 7 to the micro-reservoir 3. The first N/C flow control valve 1a opens to fill the micro-reservoir 3 with insulin from the primary reservoir 7. The second flow control valve 1b controls the isolation of the fluid path when dispensing from the micro-reservoir 3 to the infusion site and prevents unintentional delivery of insulin to the infusion site.

The controlled orifice 5, which may comprise an adjustable flow valve, is provided to allow the flow rate of insulin into the subcutaneous tissue of the patient to be calculated.

A check valve (not shown) can be optionally provided to eliminate flow back to the macro-reservoir or primary reservoir 7 during the micro-reservoir delivery cycle. Typically, such check valve would be incorporated into the system if the flow control valve N/C 1a were not part of the system.

FIGS. 9 and 10 both illustrate metering systems 1000, 1001 that can be incorporated into a MEMS chip in a manner similar to the embodiments illustrated in FIGS. 7 and 8, wherein the combination of the flow control valve N/C 1a and the micro-reservoir 3 safeguard the infusion pump engine from inadvertent insulin delivery by pre-loading and pressurizing only a safe or less-than-harmful dose of insulin medicament within the micro-reservoir 3. A fluid driver 4 in the form of a preloaded spring, a solenoid, or other fluid driver delivers incremental micro-doses from the micro-reservoir 3 to the infusion site in order to improve the accuracy of the insulin doses delivered to the infusion site to within +/−1% of the target dose. Additionally, the pressure sensors 2a, 2b illustrated in FIGS. 9 and 10 provide feedback on the fill status of the micro-reservoir 3, detect occlusion or back pressure in the infusion pump device, detect leakage in the infusion device, and detect the injection flow rate of the insulin in the infusion pump device.

Figure 11:
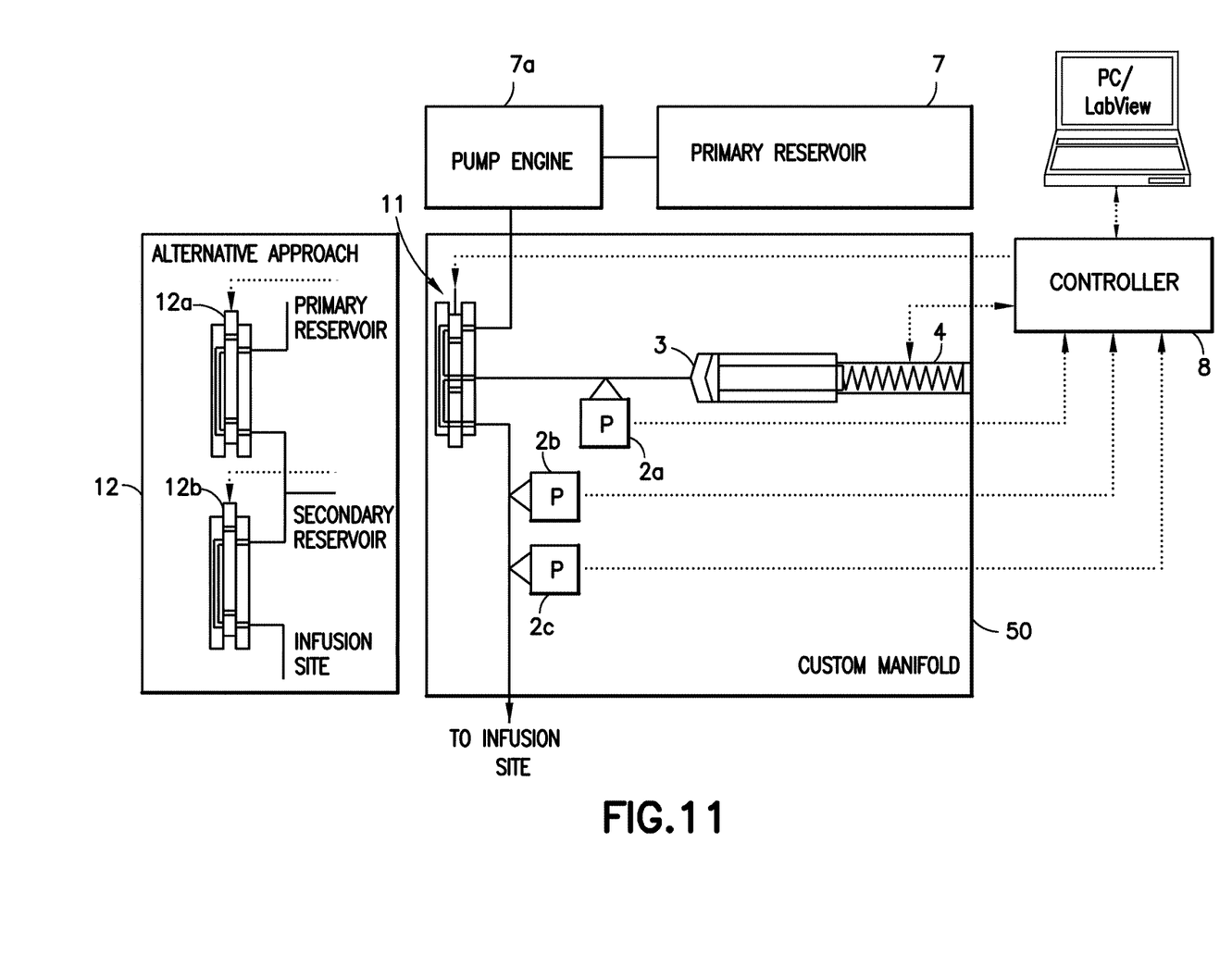
FIG. 11 depicts another illustrative alternate embodiment of an insulin infusion metering system of the present invention incorporating a MEMS actuator.

FIG. 11 illustrates another embodiment of a metering system that can be incorporated into a MEMS chip of the present invention, wherein a MEMS actuator is utilized to shift the gate of a two position gate valve 11. Specifically, when an electric potential is applied to the plates of the gate valve 11, the central plate is actuated and slides with respect to the outer plates. Depending on the position of the central plate, the gate valve 11 will allow flow from either the primary reservoir to the secondary reservoir or from the secondary reservoir to the infusion site. In the absence of an electrical potential, however, the central plate of the gate valve 11 is aligned to allow flow from the primary reservoir to the secondary reservoir, as illustrated in FIG. 11. The gate valve 11, pressure sensors 2a, 2b, 2c, micro-reservoir 3 and engine 4 and accompanying interconnects can be incorporated into a custom manifold 50 or MEMS chip. Alternately, the gate valve 11 could include a third position, such that in the absence of electrical power, all flow is blocked.

In an alternative embodiment of the present invention, a MEMS actuator is utilized to open two N/C displacement gate valves 12a and 12b, instead of the single gate valve 11, to allow flow independent control of the flow from the primary reservoir 7 to the secondary reservoir 3 and from the secondary reservoir 3 to the infusion site. Specifically, when an electric potential is applied to the plate of the N/C gate valve 12a, the central plate thereof is actuated and slides with respect to the outer plates. This causes the N/C gate valve 12a to align and open the flow channels from the primary reservoir 7 to the secondary reservoir 3. Removing the electrical power from N/C gate valve 12a shifts the central plate to the N/C position. To provide flow from the secondary reservoir 3 to the infusion site, electrical power is then applied to the central plate of the N/C gate valve 12b, and the central plate is actuated and slides with respect to the outer plates. This causes the central plate of the gate valve 12b to align and open the flow channels from the secondary reservoir 3 to the infusion site. In the absence of an electrical potential, however, the plates of the two gate valves 12a and 12b are misaligned, which blocks the flow channels and stops flow to the infusion site.

Accordingly, illustrative embodiments of the present invention provide higher levels of infusion accuracy in combination with a fail-safe metering system for an insulin infusion pump, prevent inadvertent overdosing of a patient by pre-loading and pressurizing only a safe or less-than-harmful dose of medicament in the reservoir of the metering system in the insulin infusion pump, permit the use of higher concentration drugs while abiding by industry requirements for pump engine accuracy, permit fine incremental dosing to approximate continuous infusion, and provide a low-cost metering system that is interchangeable with any type of pump engine, including pump engines with low accuracy.

The individual components used in the exemplary patch pump embodiments disclosed herein, including pump engines, fluidic assemblies, metering systems, catheter deployment assemblies, fluid reservoirs and control systems, can be based on existing designs and technologies which are known in the art. For example, pump engines, fluidic assemblies and metering systems utilizing stepper motors, shape memory alloy (SMA) actuators, piezoelectric actuators, Micro Electro Mechanical Systems (MEMS) devices, and directional control valves may be used. Fluid reservoirs may be rigid or deformable (e.g., with force applied by a movable plunger or preloaded spring).

The following U.S. and foreign patent documents, which are incorporated by reference herein, disclose exemplary components and subsystems which may be used in the practice of the present invention:

U.S. Pat. No. 5,858,001
U.S. Pat. No. 5,858,005
U.S. Pat. No. 5,957,895
U.S. Pat. No. 6,074,369
U.S. Pat. No. 6,551,276
U.S. Pat. No. 6,589,229
U.S. Pat. No. 6,656,158
U.S. Pat. No. 6,740,059
U.S. Pat. No. 6,852,104
U.S. Pat. No. 6,960,192
U.S. Pat. No. 7,052,251
U.S. Pat. No. 7,109,878
U.S. Pat. No. 7,128,727
U.S. Pat. No. 7,226,278
U.S. Pat. No. 7,250,037
U.S. Pat. No. 7,303,549
U.S. Pat. No. 7,678,079

-continued

U.S. Pat. No. 7,857,131
U.S. Pat. No. 8,021,334
US 2008/0097381
US 2009/0048563
US 2009/0062778
EP 2019206

While certain exemplary embodiments of the present invention have been shown and described herein with reference to certain preferred embodiments thereof, it will be understood by those skilled in the art that various changes in form and details may be made therein without departing from the spirit and scope of the invention as defined in the appended claims and their equivalents.

What is claimed is:

1. An infusion pump system for dispensing a liquid medication, comprising:
   a first reservoir having a first cross-sectional area for storing the liquid medication and a pump engine for moving a plunger within the first cross-sectional area;
   a second reservoir having a second cross-sectional area smaller than the first cross-sectional area, and a fluid driver for moving a plunger within the second cross-sectional area of the second reservoir for storing the liquid medication received from the first reservoir;
   a first valve configured to control the flow of the liquid medication from the first reservoir to the second reservoir allowing the fluid to move from the first reservoir to the second reservoir and increase the volume of the second reservoir to receive the liquid medication from the first reservoir;
   a second valve configured to control the flow of the liquid medication from the second reservoir to an infusion site when fluid driver drives fluid from the second reservoir;
   wherein the first valve is selectively opened or closed to admit the liquid medication from the first reservoir to the second reservoir; and
   wherein the second valve is selectively opened or closed to dispense the liquid medication from the second reservoir to the infusion site.

2. The infusion pump system as claimed in claim 1, further comprising a third valve for controlling the flow rate of the liquid medication to the infusion site.

3. The infusion pump system as claimed in claim 2, wherein the third valve comprises an adjustable flow valve comprising an adjustable orifice through which the liquid medication flows to the infusion site.

4. The infusion pump system as claimed in claim 2, further comprising a Micro Electro Mechanical Systems (MEMS) chip unit comprising the first valve, the second valve and the third valve.

5. The infusion pump system, as claimed in claim 2, further comprising:
   a first sensor for sensing and monitoring fluid line pressure to inform a controller when the second reservoir is filled to an acceptable level, the controller stopping the first fluid driver when the second reservoir reaches the acceptable level.

6. The infusion pump system as claimed in claim 5, wherein the first sensor comprises a pressure sensor.

7. The infusion pump system as claimed in claim 5, wherein the first sensor is configured to:
   detect pressure decay;

determine where a leak in the fluidic system exists by opening one or more of the first, the second, and the third the valves individually;

determine the fill state of the first or second reservoirs; and/or determine if partial or complete occlusion exists in the system.

8. The infusion pump system as claimed in claim 2, further comprising:

a second sensor for informing a controller when the amount of the liquid medication in the second reservoir is at a low or acceptable level, the controller activating the first fluid driver to fill the second reservoir when the amount of the liquid medication in the second reservoir is at a low or acceptable level and stopping the first fluid driver when the second reservoir reaches the acceptable level.

9. The infusion pump system as claimed in claim 8, wherein the second sensor comprises a position sensor configured to detect the position of a plunger in the second reservoir.

10. The infusion pump system as claimed in claim 2, wherein incremental dosing of the liquid medication from the second reservoir to the infusion site occurs when the first valve is closed, the second valve is open, and the third valve is controlling the flow rate of the liquid medication to the infusion site.

11. The infusion pump system, as claimed in claim 2, wherein the first valve comprises a flow control valve.

12. The infusion pump system, as claimed in claim 2 further comprising:

one or more sensors for detecting occlusion or back pressure within the infusion pump system;

one or more sensors for detecting presence of bubbles in a delivery line of the infusion pump system;

one or more sensors for detecting a fill status of the secondary reservoir of the infusion pump system;

one or more sensors for detecting leakage in the infusion pump system; and/or one or more sensors for measuring a flow rate of the liquid medication in the infusion pump system.

13. The infusion pump system as claimed in claim 2, wherein the second reservoir, the fluid driver, the first valve, the second valve, and associated fluid connectors comprise a metering system.

14. The infusion pump system as claimed in claim 2, further comprising:

a second sensor for sensing and monitoring fluid line pressure between the first reservoir and the second reservoir and informing a controller when the second reservoir is filled to an acceptable level, the controller stopping the at least one fluid driver from exerting pressure on the first reservoir when the second reservoir reaches the acceptable threshold.

15. The infusion pump system as claimed in claim 2, wherein the first valve and the second valve each comprise a flow control valve.

16. The infusion pump system as claimed in claim 2, further comprising:

a plurality of pressure sensors connected to the second reservoir to provide feedback on the fill status of the second reservoir, to detect occlusion in the infusion pump system, to detect back pressure in the infusion pump system, and/or to detect a flow rate of the liquid medication into the infusion site.

17. The infusion pump system as claimed in claim 2, further comprising a Micro Electro Mechanical Systems (MEMS) chip comprising at least one of the first, second and third valves.

18. The infusion pump system as claimed in claim 17, wherein the MEMS chip further comprises the second reservoir.

19. The infusion pump system as claimed in claim 17, further wherein the MEMS chip further comprises the first sensor.

20. The infusion pump system as claimed in claim 1, wherein the first valve comprises a check valve, and the second valve comprises a directional control valve.

21. The infusion pump system as claimed in claim 1, wherein the second reservoir, the fluid driver, the first valve, the second valve, the third valve and one or more fluid connectors comprise a metering system.

22. The infusion pump system as claimed in claim 1, wherein the first reservoir comprises a syringe-type reservoir.

23. The infusion pump system as claimed in claim 1, wherein the maximum storage capacity for the liquid medication in the second reservoir is a safe or less than harmful dose to a user.

24. The infusion pump system as claimed in claim 1, wherein the maximum storage capacity of the liquid medication in the first reservoir is greater than that of the second reservoir.

25. The infusion pump system as claimed in claim 1, wherein at least one of the first and second valves is controlled by applying electrical potentials.

* * * * *